US005321144A

United States Patent [19]

Narula et al.

[11] Patent Number: 5,321,144

[45] Date of Patent: Jun. 14, 1994

[54] P-METHYLENEDIOXYPHENYL PROPIONITRILE DERIVATIVES, PROCESS FOR PRODUCING SAME, INTERMEDIATES USED IN SAID PROCESS AND ORGANOLEPTIC USES OF SAID DERIVATIVES AND INTERMEDIATES

[75] Inventors: Anubhav P. S. Narula, Hazlet; John J. De Virgilio, Red Bank; Charles E. J. Beck, Summit; Marie R. Hanna, Keyport, all of N.J.; Jan T. Van Elst, Bilthoven, Netherlands

[73] Assignee: International Flavors & Fragrances Inc., New York, N.Y.

[21] Appl. No.: 92,465

[22] Filed: Jul. 16, 1993

Related U.S. Application Data

[62] Division of Ser. No. 6,605, Jan. 21, 1993.

[51] Int. Cl.[5] .......... C07D 317/28

[52] U.S. Cl. .......... 549/442

[58] Field of Search .......... 549/442

[56] References Cited

U.S. PATENT DOCUMENTS 5,143,899 9/1992 Narula et al. .......... 512/6

OTHER PUBLICATIONS

Semmelhack and Barger, J. Am. Chem. Soc., 1980, 102(26) pp. 7765–7774, "Photostimulated Nucleophilic Aromatic Substitution for Halides with Carbon Nucleophiles. Preparative and Mechanistic Aspects".

*Primary Examiner*—Nicky Chan

*Attorney, Agent, or Firm*—Arthur L. Liberman

[57] ABSTRACT

Described are p-methylenedioxyphenyl propionitrile and propiohydroxylamine derivatives defined according to the generic structure:

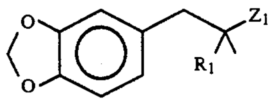

wherein $Z_1$ represents the moiety:

$-(C\equiv N)$ and the moiety:

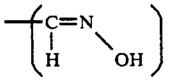

and $R_1$ is hydrogen or methyl and also having the generic structure:

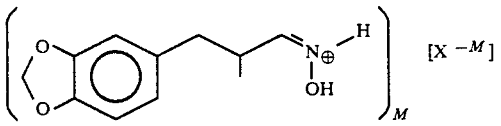

wherein X is $HSO_4^-$; $SO_4$; $^=Cl^-$; $Br^-$; $PO_4^=$; $H_2PO_4^-$; and $HPO_4^=$; and the process of preparing these compounds.

1 Claim, 11 Drawing Sheets

G C PROFILE FOR EXAMPLE I.

IR SPECTRUM FOR EXAMPLE I.

G C PROFILE FOR EXAMPLE II.

I R SPECTRUM FOR EXAMPLE II.

G C SPECTRUM FOR EXAMPLE III.

I R SPECTRUM FOR EXAMPLE III.

P-METHYLENEDIOXYPHENYL PROPIONITRILE DERIVATIVES, PROCESS FOR PRODUCING SAME, INTERMEDIATES USED IN SAID PROCESS AND ORGANOLEPTIC USES OF SAID DERIVATIVES AND INTERMEDIATES

This is a divisional of application Ser. No. 006,605, filed Jan. 21, 1993, pending.

BACKGROUND OF THE INVENTION

Our invention relates to p-methylenedioxyphenyl propionitrile and propiohydroxylamine derivatives defined according to the structures:

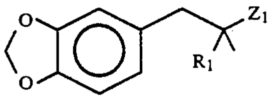

and

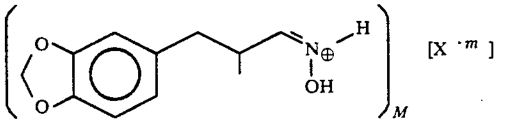

wherein $R_1$ is hydrogen or methyl;

$Z_1$ is one of the moieties:

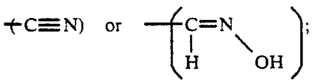

M is 1, 2 or 3; and

X is one of the anions:

$HSO_4^-$;

$SO_4^=$;

$Cl^-$;

$Br^-$;

$PO_4^{\equiv}$;

$H_2PO_4^-$; and $HPO_4^=$.

Our invention also covers the genus of compounds having the structure:

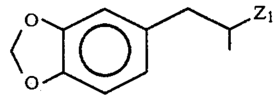

as well as the genus of compounds having the structure:

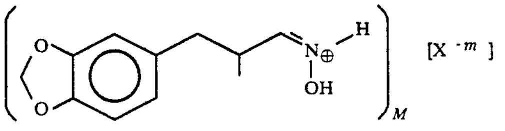

as novel compounds. Our invention also covers the uses of the compounds having the structures:

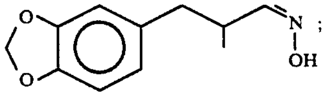

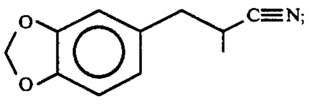

and

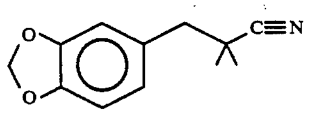

for their organoleptic (e.g., perfumery) properties.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting intense substantive sweet, anisic, ozoney, ylang, geranium, melony, basil, floral and muguet aromas with sweet, anisic, ylang and geranium topnotes are highly desirable in several types of perfume compositions, perfumed articles and colognes (e.g., piney fragrances).

The perfume uses of nitrile-containing derivatives which contain phenyl moieties are well known in the prior art. Thus, the compounds defined according to the structure:

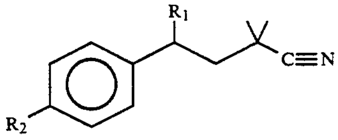

wherein $R_1$ and $R_2$ are the same or different and each represents hydrogen or methyl are disclosed in U.S. Pat. No. 5,143,899 issued on Sep. 1, 1992 (title "Process For Preparing Phenyl Butyronitriles And Perfumery Use Of 2,2-Dimethyl-4-Phenyl Valeronitrile"). Other perfume uses of nitrile-containing derivatives which also contain phenyl moieites are shown in U.S. Pat. No. 4,837,351 issued on Jun. 6, 1989 wherein it is indicated that the compound having the structure:

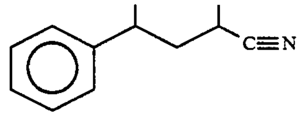

has a powerful, fresh, fruity, floral odor note accompanied by a citrus, green topnote. Furthermore, U.S. Pat. No. 3,325,369 discloses the use of cinnamonitrile as a material useful in augmenting or enhancing the aroma of perfume compositions.

Other nitriles containing gem-dimethyl moieties "alpha" to the cyanide moiety are disclosed in Blumenthal, et al, U.S. Pat. No. 3,168,550 issued on Feb. 2, 1965.

Nothing in the prior art discloses the use in perfumery of the p-methylenedioxyphenyl propionitrile and propiohydroxylamine derivatives of our invention.

However, the compound having the structure:

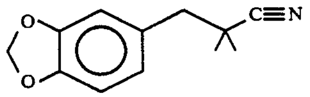

is disclosed as a chemical intermediate in the article by Semmelhack and Bargar, J.Am.Chem. Soc. 1980, 102(26) at pages 7765-7774 (abstracted at Chemical Abstracts Volume 94:3607e); (title "Photostimulated Nucleophilic Aromatic Substitution For Halides with Carbon Nucleophiles. Preparative and Mechanistic Aspects").

Nothing in the prior art, however, discloses the perfumery uses of the p-methylenedioxyphenyl propionitrile and propiohydroxylamine derivatives of our invention and nothing shows the use of the intermediates of our invention in the processes of our invention.

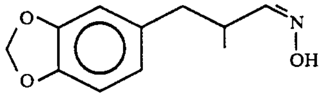

(Conditions: SE-30 column programmed at 150°-220° C. at 8° C. per minute).

Figure 2:
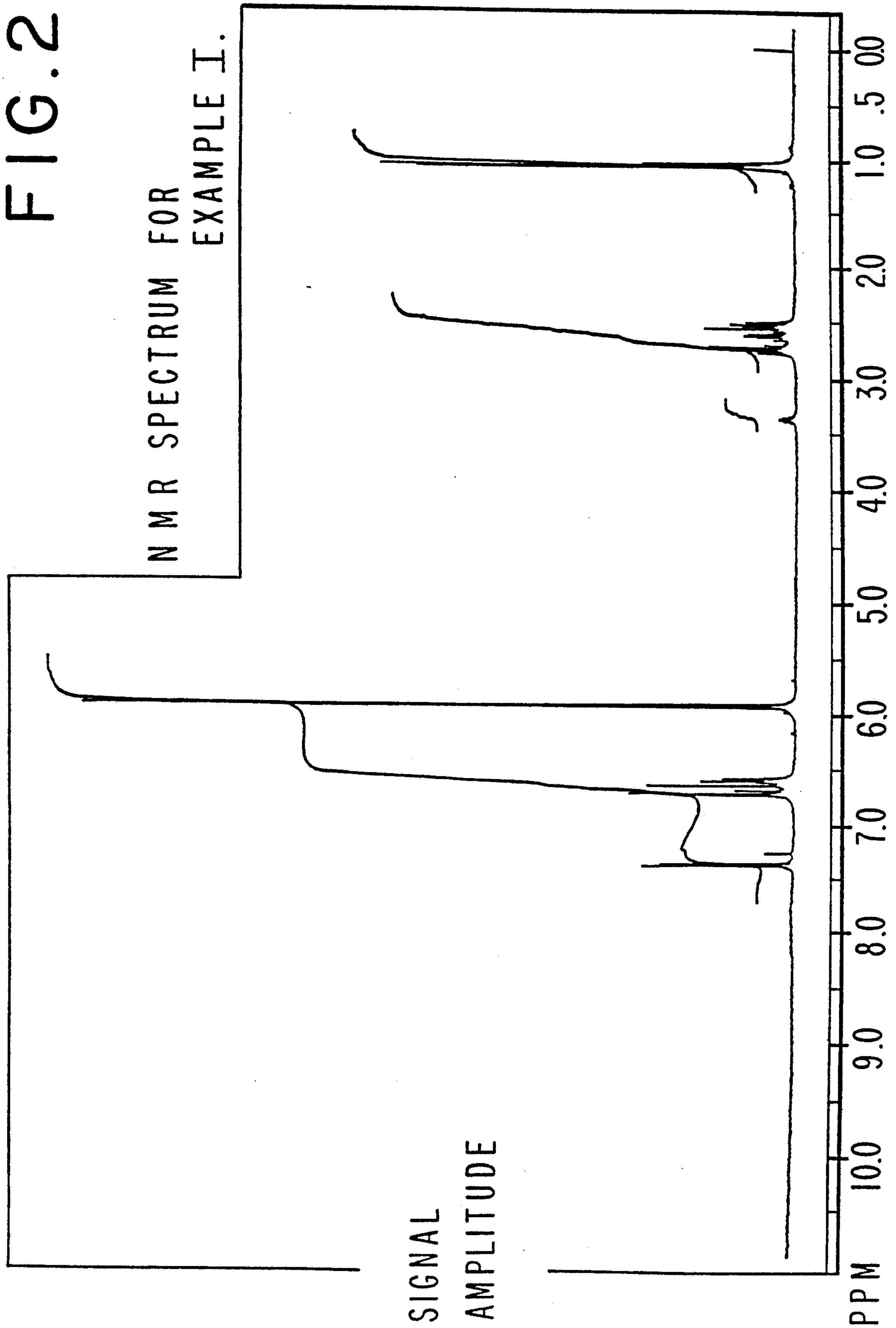

FIG. 2 is the NMR spectrum for the compound having the structure:

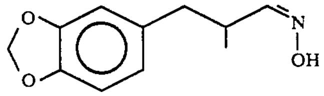

produced according to Example I.

Figure 3:
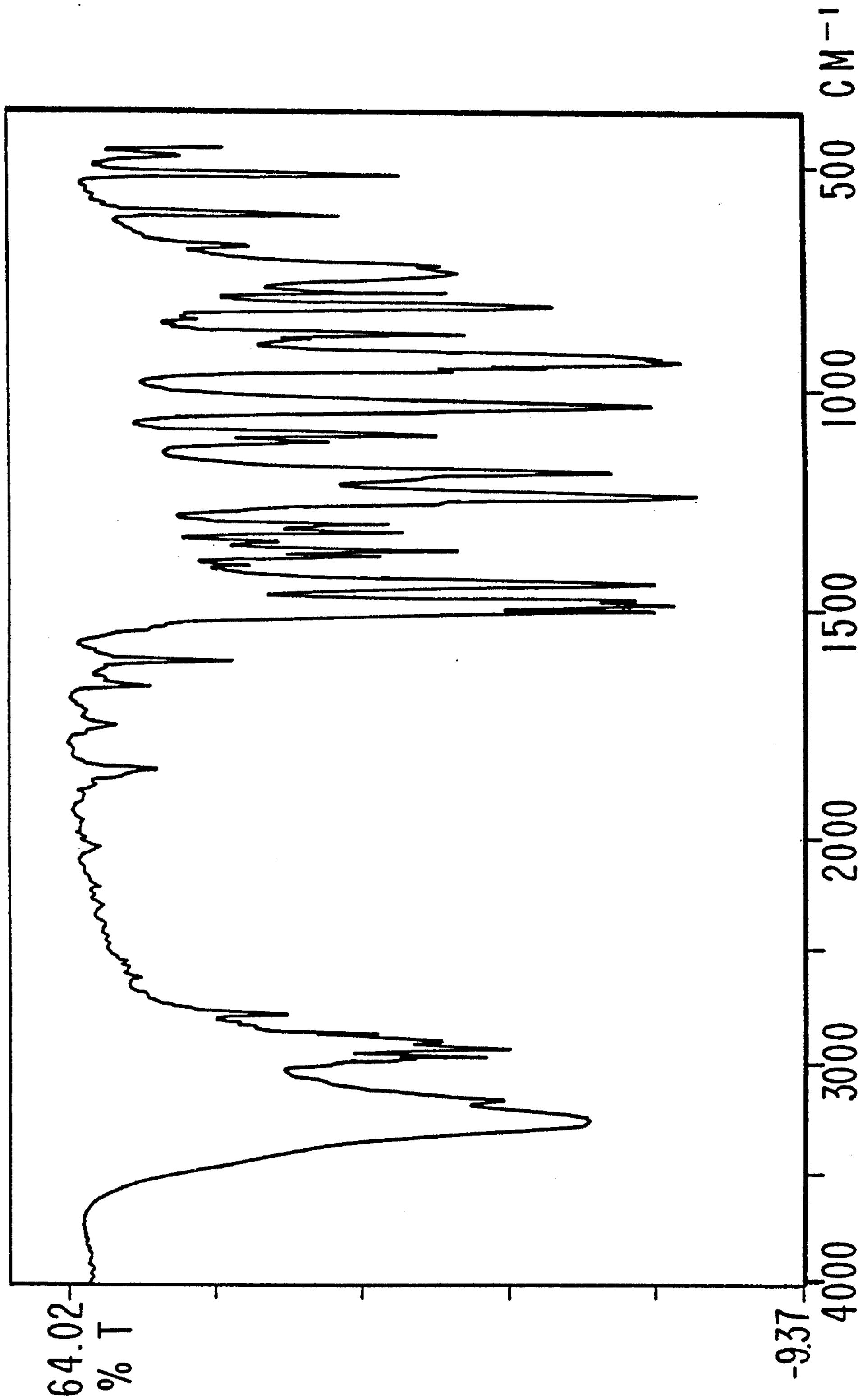

FIG. 3 is the infra-red spectrum for the compound having the structure:

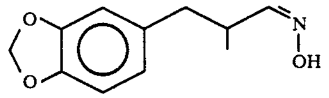

produced according to Example I.

Figure 4:
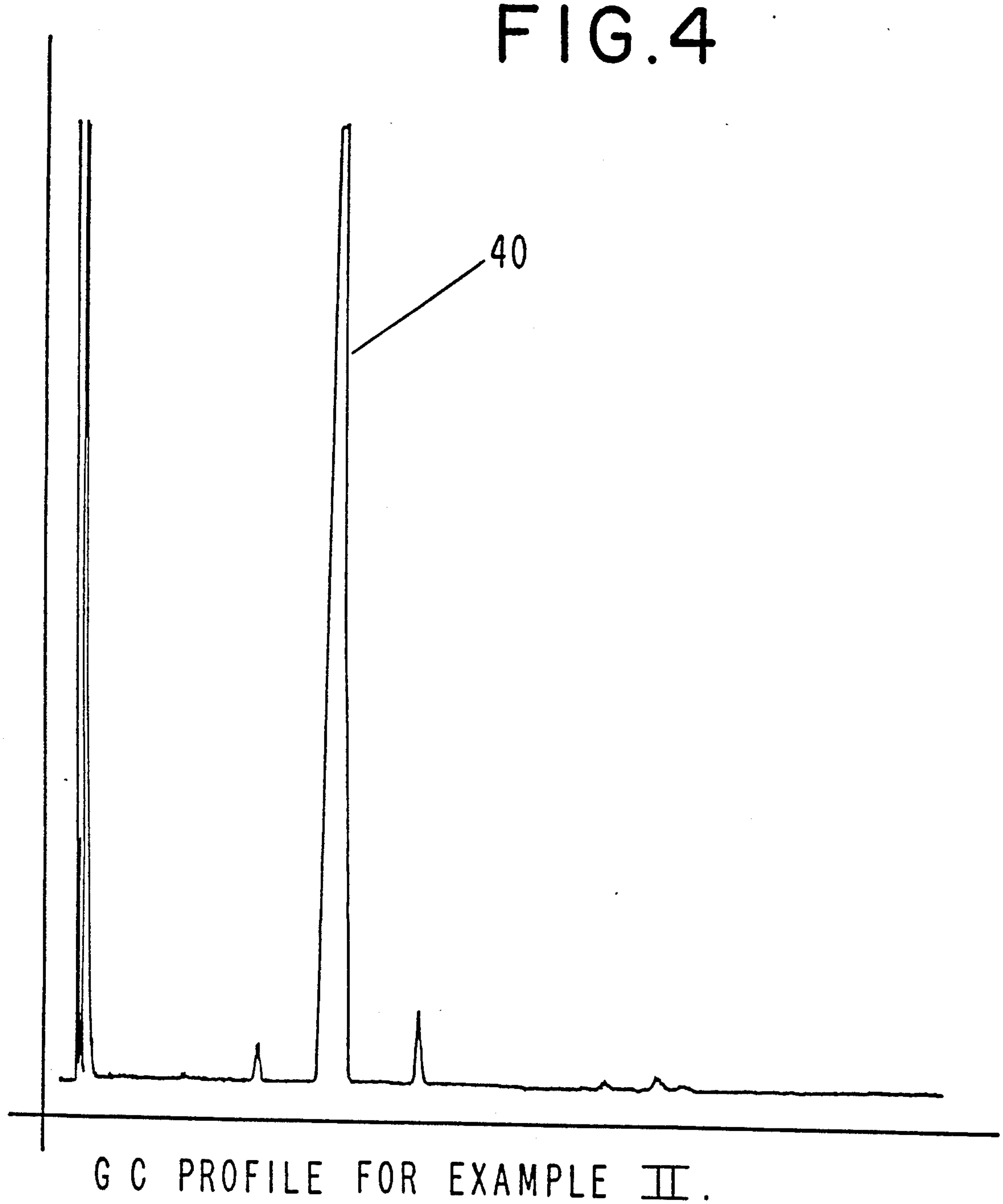

FIG. 4 is the GC spectrum for the reaction product of Example II containing the compound having the structure:

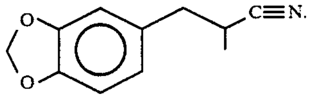

Figure 5:
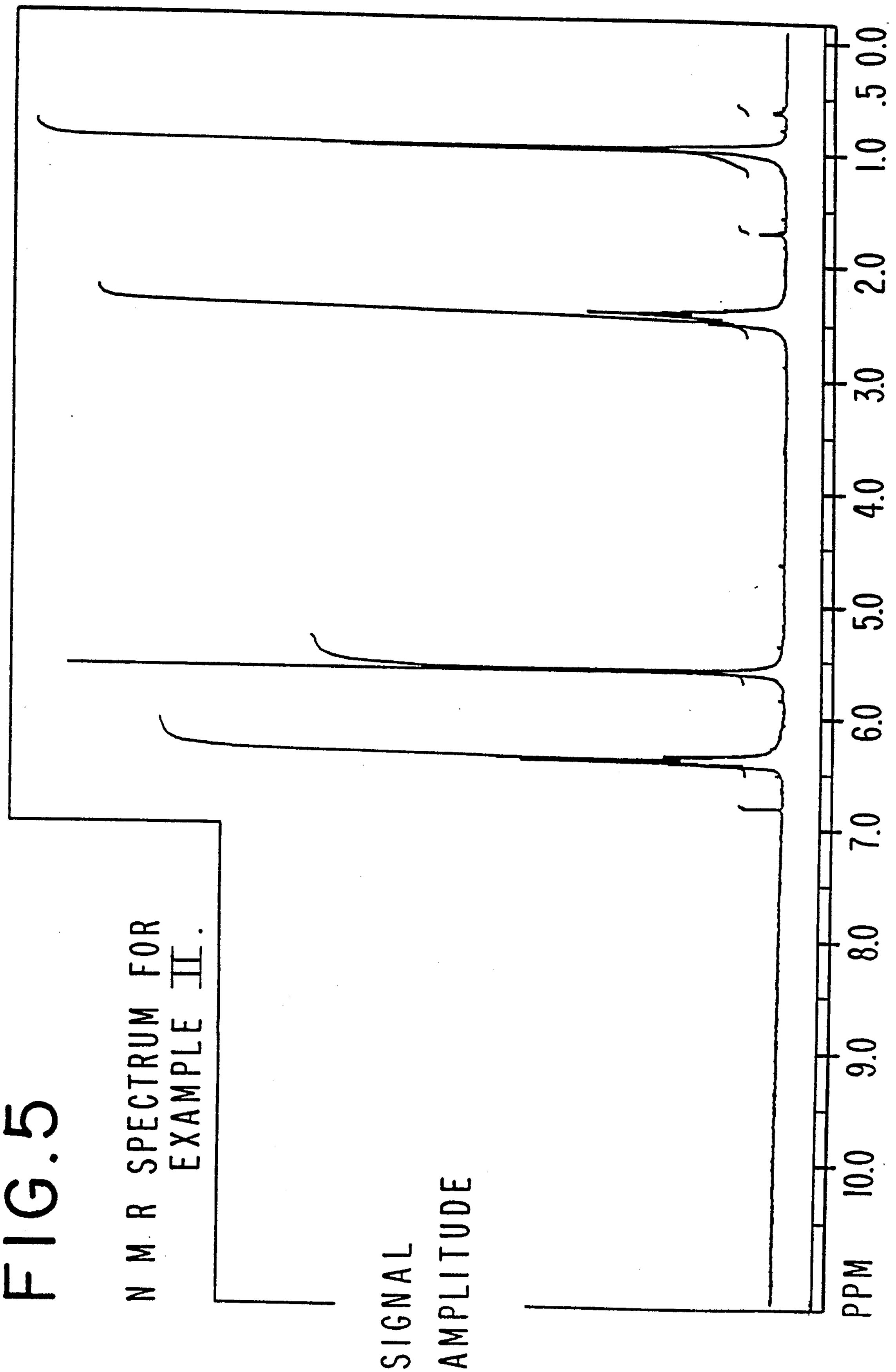

FIG. 5 is the NMR spectrum for the compound having the structure:

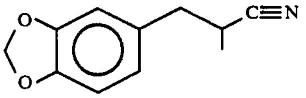

produced according to Example II.

Figure 6:
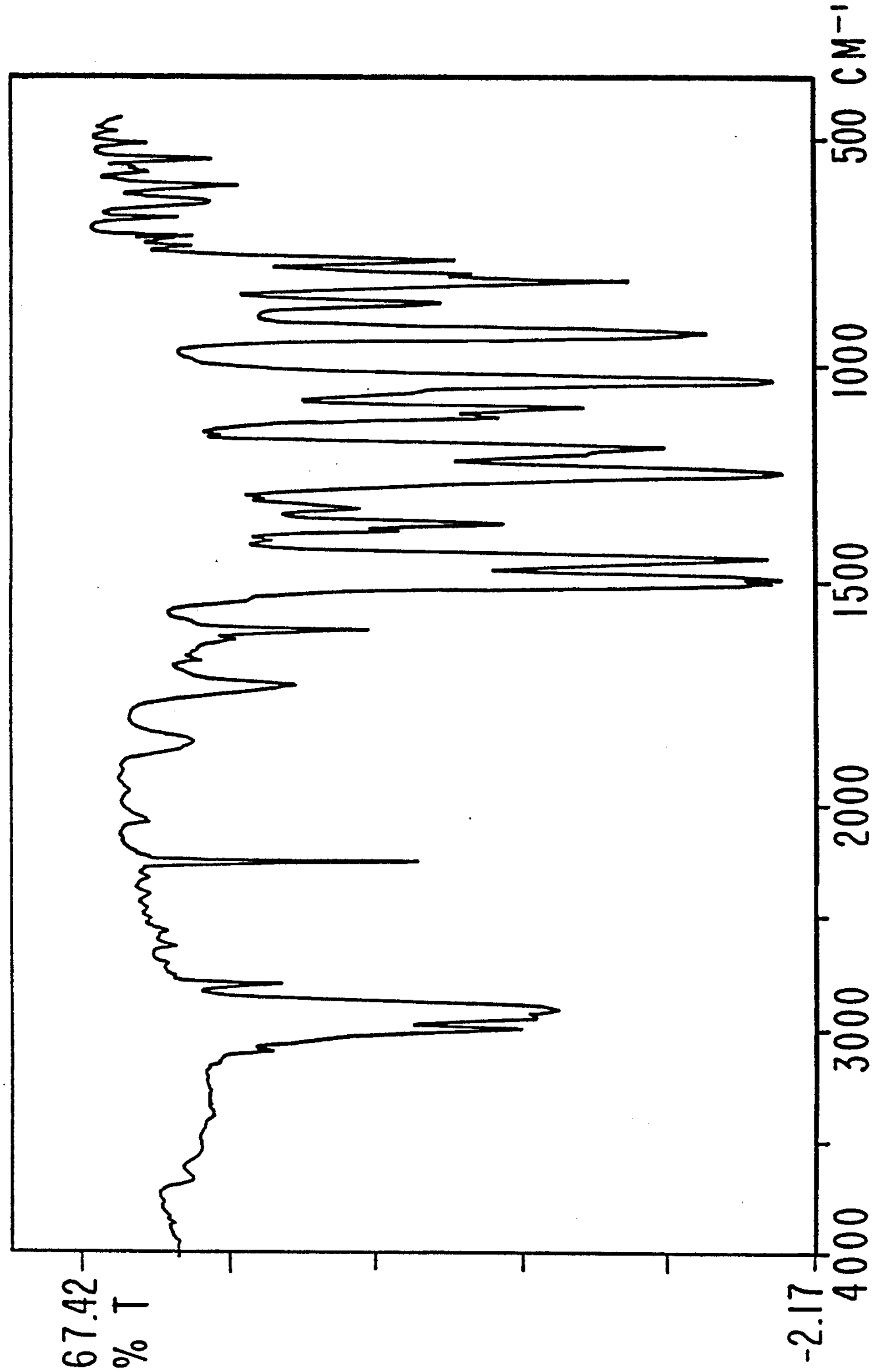

FIG. 6 is the infra-red spectrum for the compound having the structure:

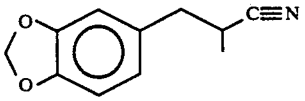

produced according to Example II.

Figure 7:
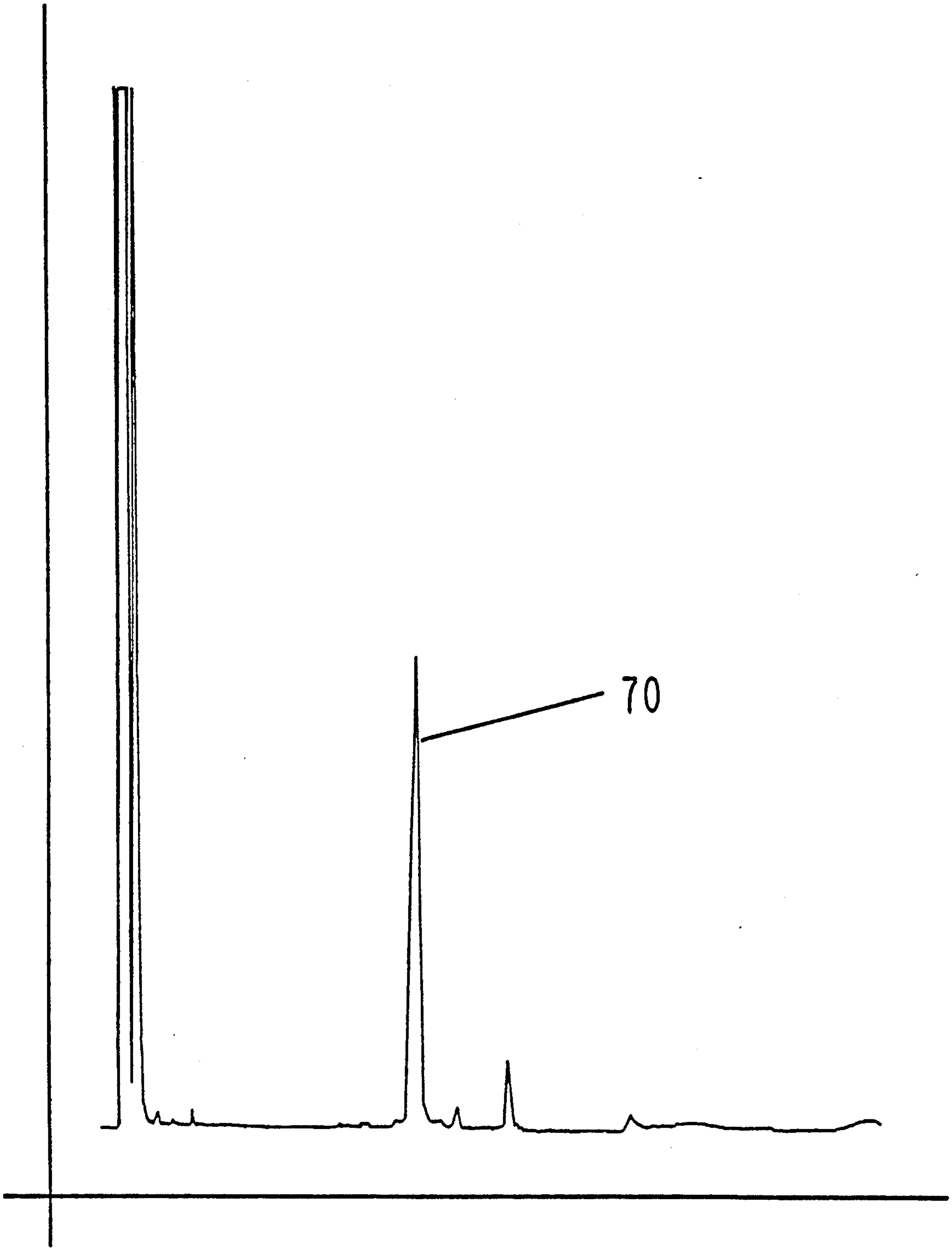

FIG. 7 is the GC spectrum for the compound having the structure:

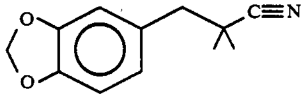

produced according to Example III (Conditions: SE-30 column programmed at 150°-220° C. at 8° C. per minute).

Figure 8:
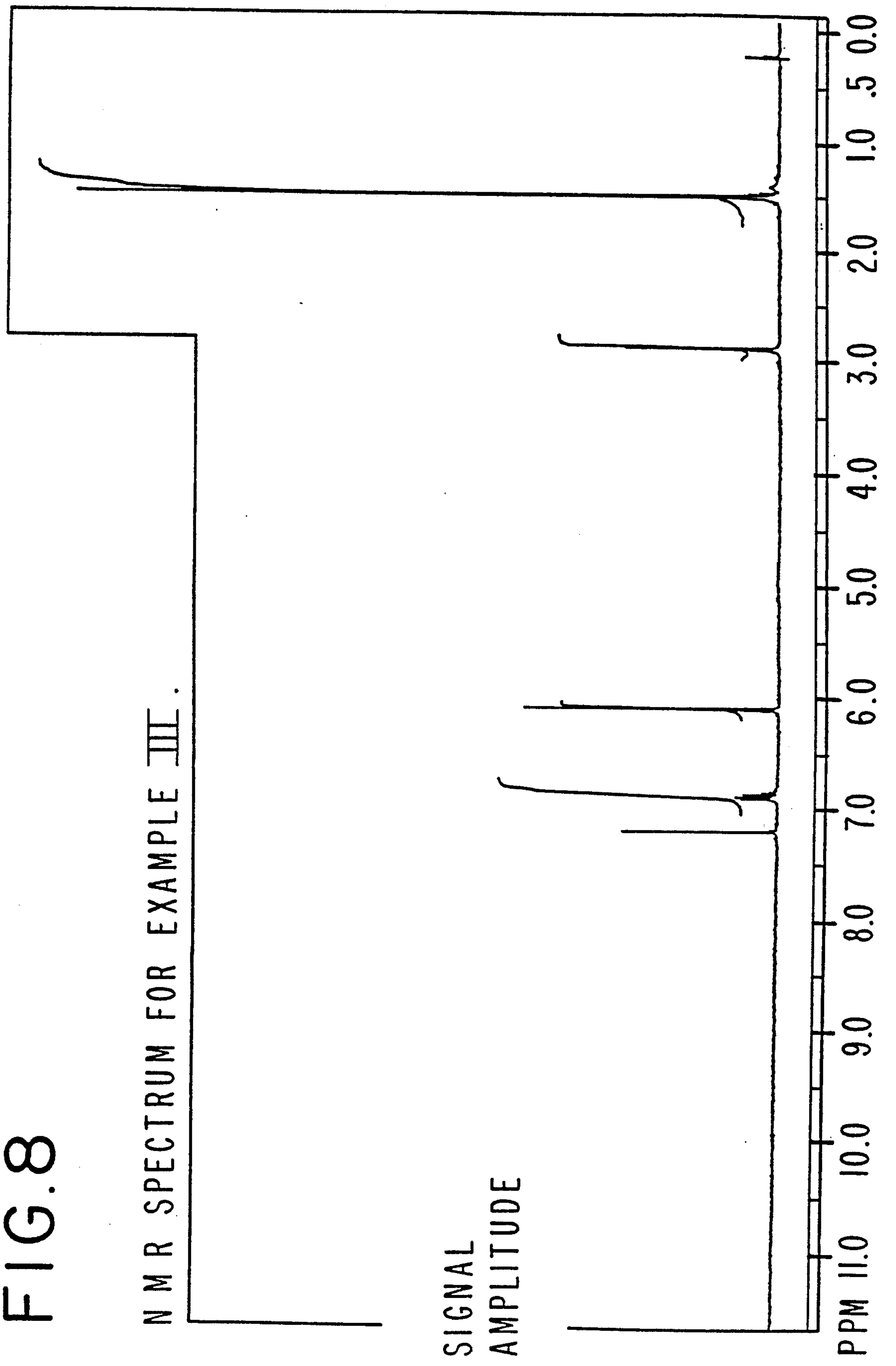

FIG. 8 is the NMR spectrum for the compound having the structure:

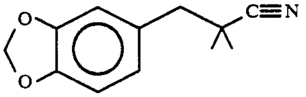

produced according to Example III.

Figure 9:
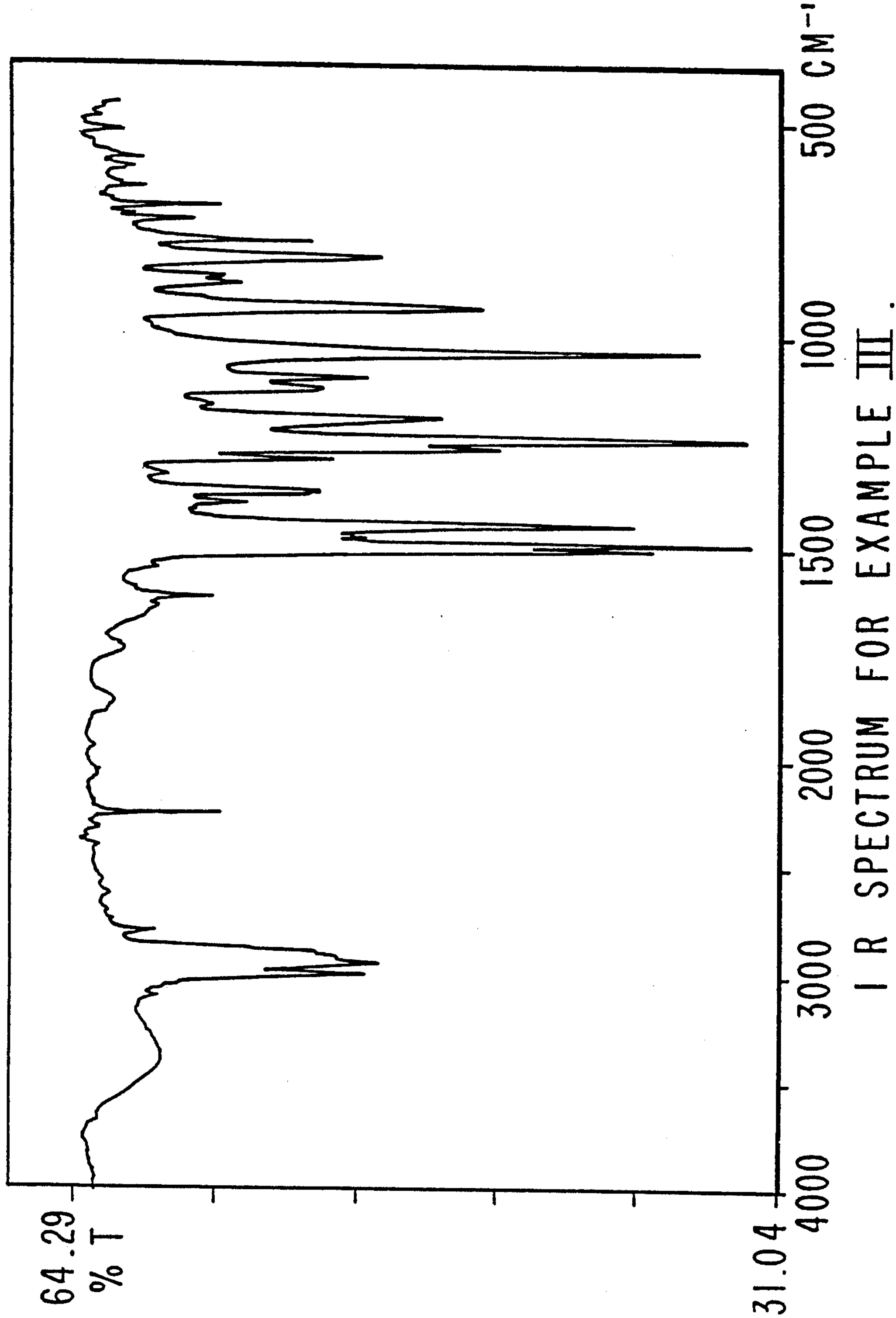

FIG. 9 is the infra-red spectrum for the compound having the structure:

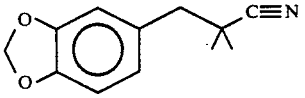

produced according to Example III.

Figure 10:
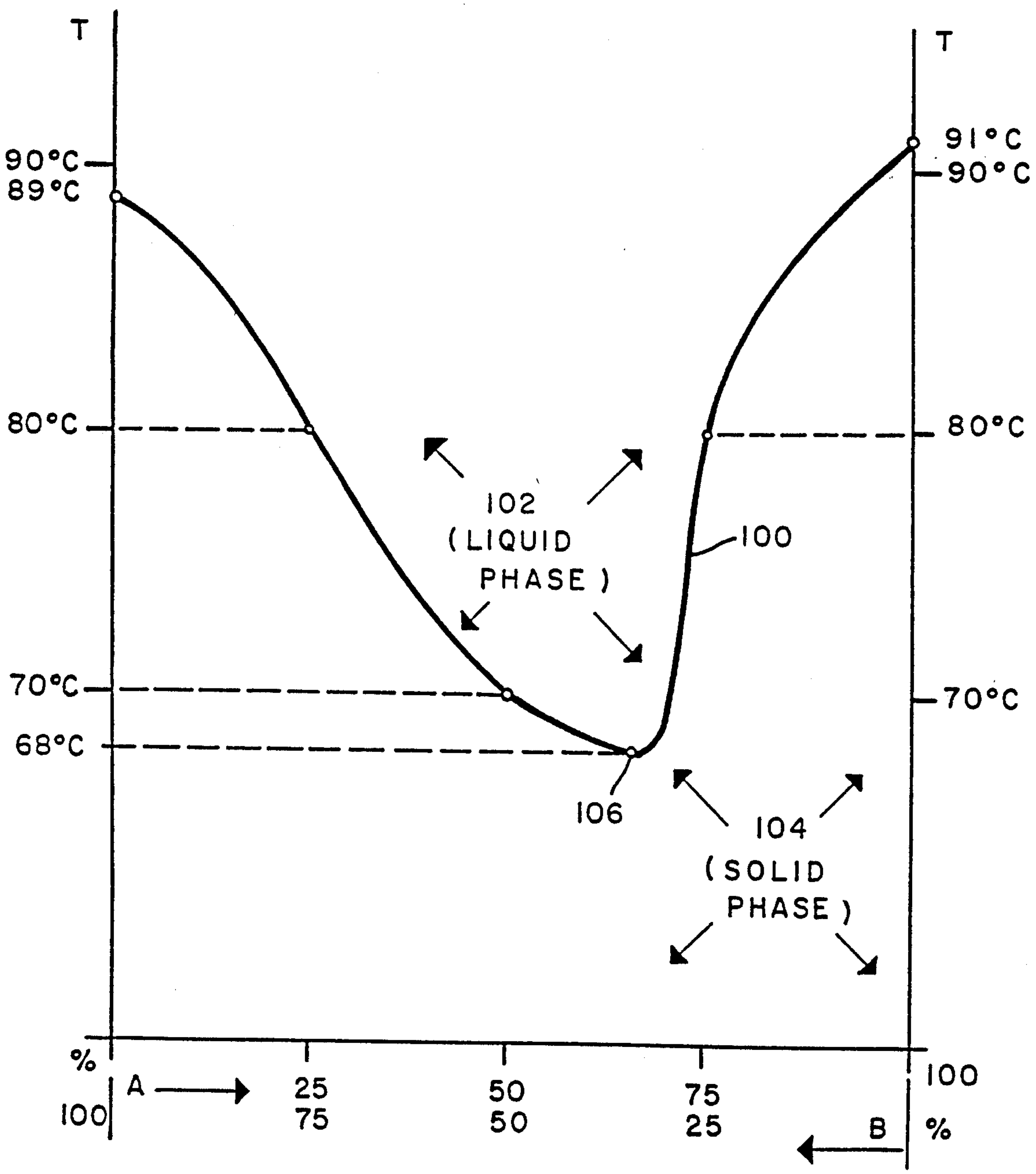

FIG. 10 is a temperature-composition diagram showing a solid and liquid phase boundary for mixtures of the compound having the structure:

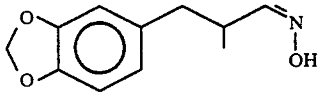

with the compound having the structure:

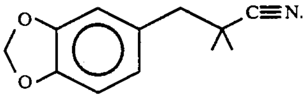

Figure 11:
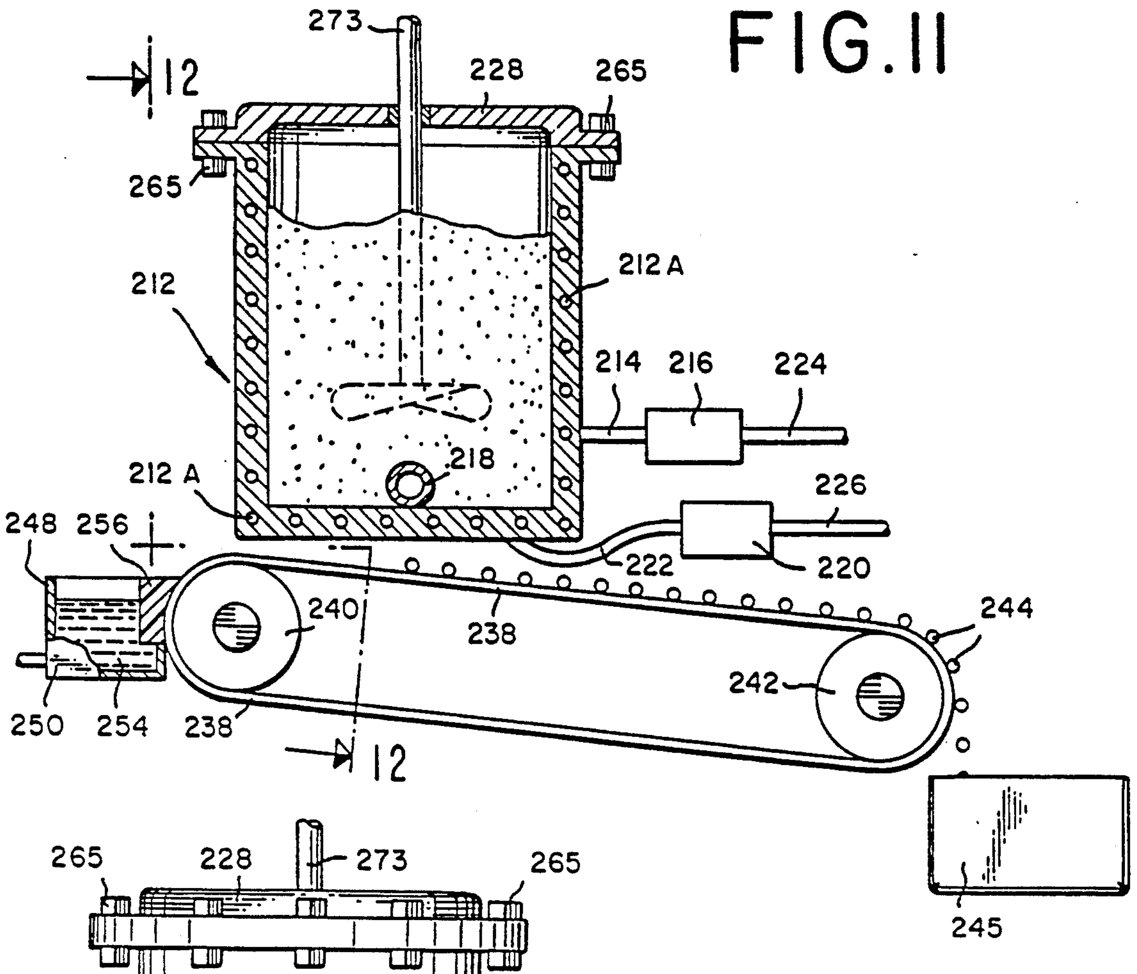

FIG. 11 represents a cut-away side elevation view of apparatus used in forming performed polymers which contain imbedded therein certain p-methylenedioxyphenyl propionitrile and propiohydroxylamine derivatives of our invention including those having the structures:

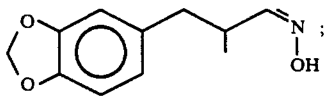

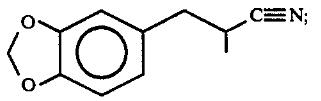

and

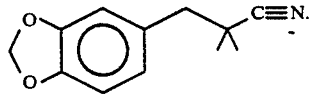

Figure 12:
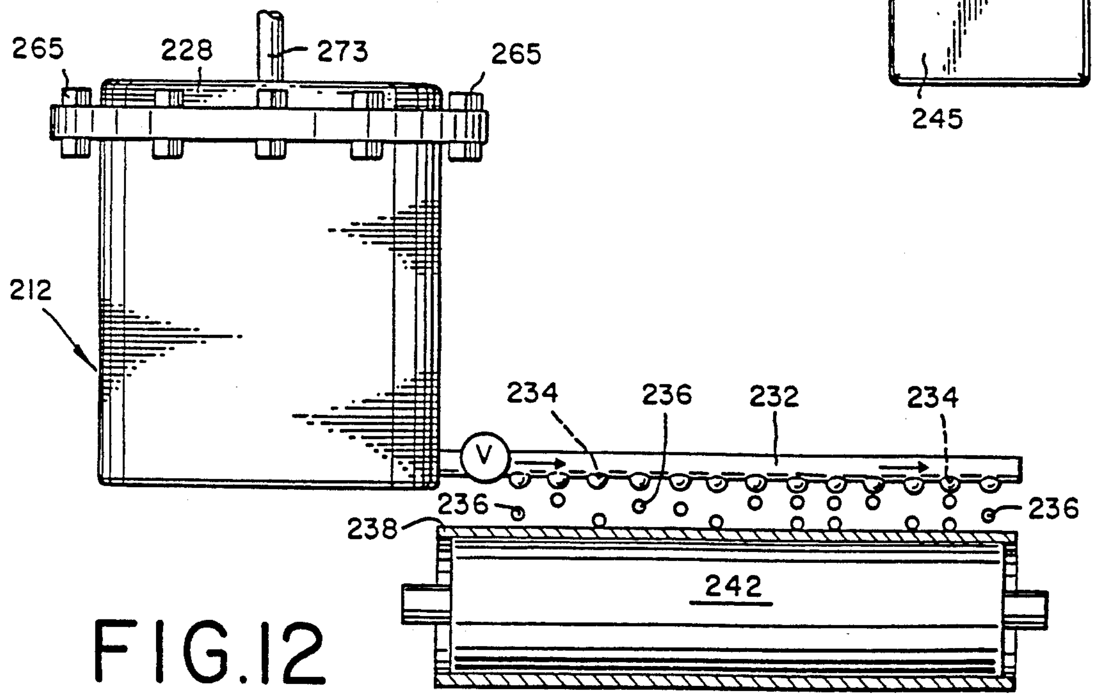

FIG. 12 is a front view of the apparatus of FIG. 11 looking in the direction of the arrows.

DETAILED DESCRIPTION OF THE DRAWINGS

Figure 1:
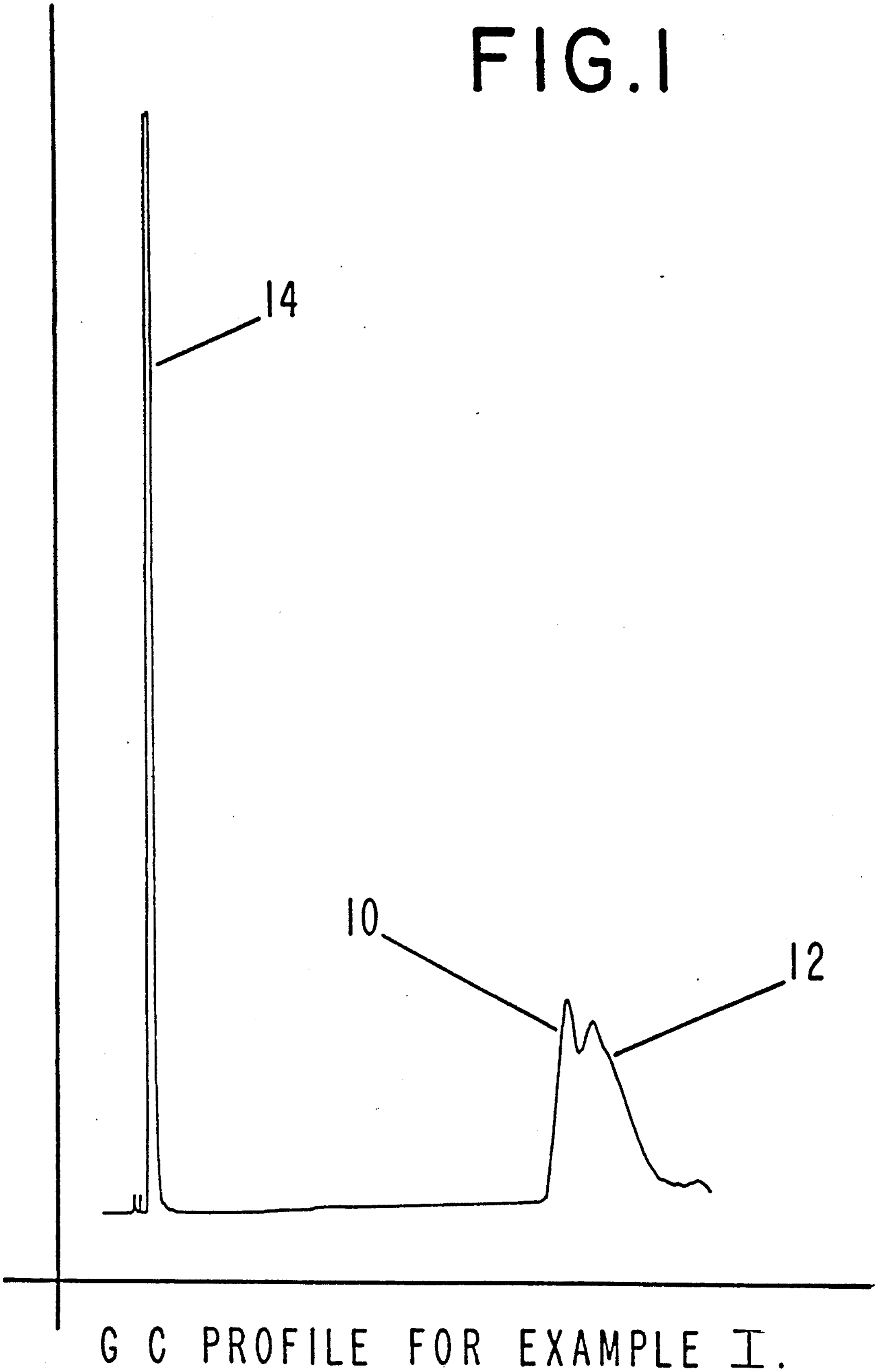
FIG. 1 is the GC spectrum for the reaction product of Example I containing the compound having the structure.

FIG. 1 is the GC spectrum for the reaction product of Example I (Conditions: SE-30 column programmed at 150°-220° C. at 8° C. per minute) 0.5 hours after the beginning of the reaction. The peaks indicated by reference numerals 10 and 12 are the peaks for the compound having the structure:

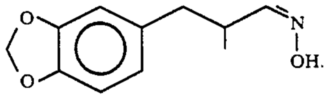

The peak indicated by reference numeral 14 is the peak for the solvent, acetone.

FIG. 4 is the GC spectrum for the reaction product of Example II containing the compound having the structure:

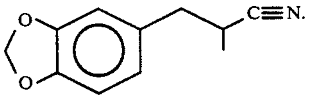

The peak indicated by reference numeral 40 is the peak for the compound having the structure:

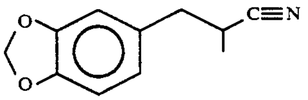

(Conditions: SE-30 column programmed at 150°-220° C. at 8° C. per minute).

FIG. 7 is the GC spectrum for the reaction product of Example III containing the compound having the structure:

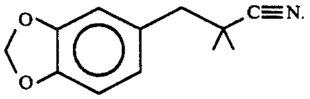

The peak indicated by reference numeral 70 is the peak for the compound having the structure:

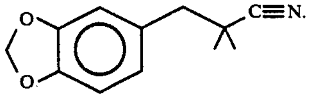

(Conditions: SE-30 column programmed at 150°-220° C. at 8° C. per minute).

FIG. 10 is a temperature versus composition graph showing liquid phase versus solid phase for compositions containing the compounds having the structure:

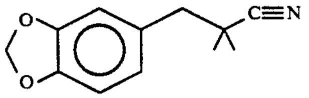

(indicated by the letter "A") and the compound having the structure:

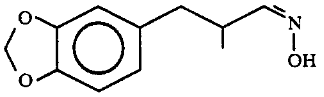

(indicated by the letter "B"). The graph is indicated by the reference numeral 100. The area indicated by the reference numeral 102 is the area for the liquid phase. The area indicated by reference numeral 104 is the area for the solid phase. The point indicated by reference numeral 106 is a eutectic point.

Referring to FIGS. 11 and 12, there is provided a process for forming scented polymer elements (wherein the polymer may be a thermoplastic polymer such as a low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles whicy may be perfumed (and, further, which may be exposed to chlorine bleaches). This process comprises heating the polymer or mixture of polymers to the melting point of said polymer or mixture of polymers, e.g. 250° C. in the case of low density polyethylene. The lower most portion of the container is maintained at a slightly lower temperature and the material in the container is taken off at such location for delivery through the conduit. Thus, referring to FIGS. 11 and 12, in particular, the apparatus used in producing such elements comprises a device for forming the polymer containing the perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the materials having the structures:

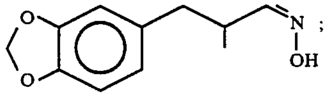

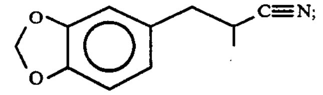

and/or

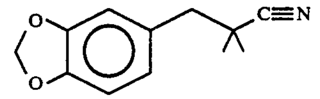

of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains at least one of the compounds having the structures:

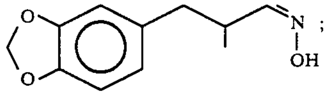

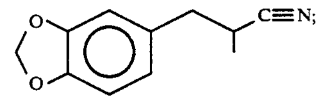

and/or

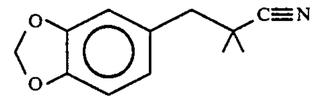

of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter the valve "V" is opened permitting the mass to flow outwardly through conduit 232 having a multiplicity of orifices 234 adjacent to the lower side thereof. The outer end of the conduit 232 is closed so that the liquid polymer in in itimate admixture with at least one of the compounds having the structures:

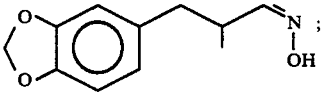

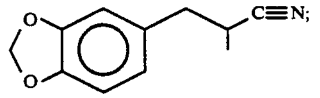

and/or

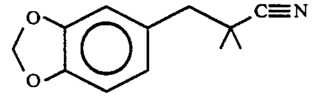

of our invention and one or more other substances, will continuously drop through the orifices 234 downwardly from the conduit 232. During this time, the temperature of the polymer intimately admixed with the perfumery substance in the container 212 is accurately controlled so that a temperature in a range of from about 240°–250° C., for example, (in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is at least one of the compounds having the structures:

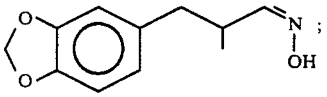

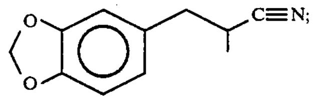

and/or

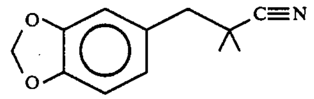

of our invention through the orifices 234 at a rate which insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The present invention provides p-methylenedioxyphenyl propionitrile and propiohydroxylamine derivatives as well as the uses of a number of such p-methylenedioxyphenyl propionitrile and propiohydroxylamine derivatives having the structures:

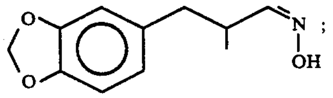

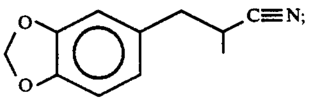

and

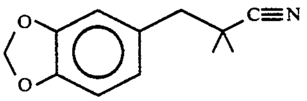

in augmenting or enhancing or imparting aroma to or in perfume compositions, perfumed articles and colognes.

The p-methylenedioxyphenyl propionitrile and propiohydroxylamine derivatives of our invention are those defined according to the generic structure:

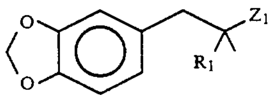

wherein $R_1$ is hydrogen or methyl and $Z_1$ is one of the moieties:

 or 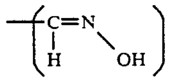

and compounds defined according to the generic structure:

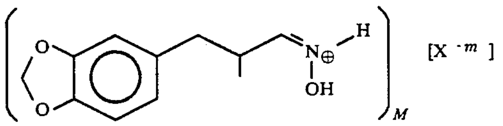

wherein M is an integer selected from the group consisting of 1, 2 or 3; and X is an anion which is one of the anions:

$HSO_4^-$; $SO_4^=$; $Cl^-$; $Br^-$; $PO_4^{\equiv}$; $H_2PO_4^-$; and $HPO_4^=$.

The compounds having the structures:

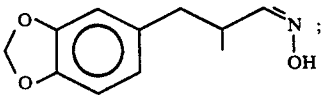

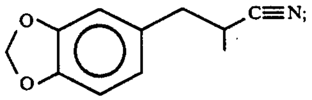

and

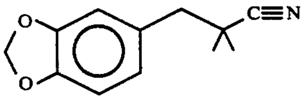

have uses in augmenting or enhancing the aroma of perfume compositions, colognes and perfumed articles, including but not limited to perfumed polymers, cosmetic powders, anionic, cationic, nonionic or switterionic detergents, fabric softener compositions, fabric softener articles including drier-added fabric softener articles (e.g., BOUNCE ® marketed by the Proctor & Gamble Company of Cincinnati, Ohio). Of particular significance in our invention are liquid mixtures of the compounds having the structures:

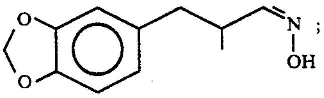

and

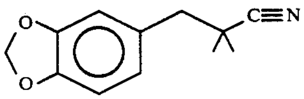

since these two materials are themselves crystalline solids. When admixed and heated, the two materials form a eutectic mixture at 68° C. as shown by FIG. 10 described, supra.

Thus, the compounds having the structures:

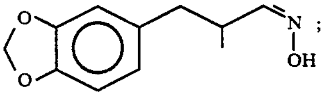

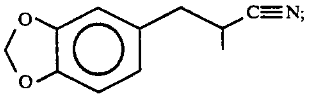

and

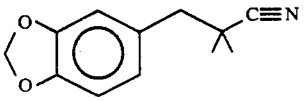

as well as various mixtures thereof including the liquid mixtures of compounds having the structures:

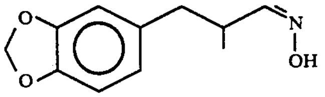

and

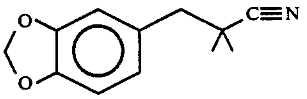

including its eutectic mixture are capable of imparting, augmenting or enhancing sweet, anisic, ozoney, ylang, geranium, melony, basil, floral and muguet aromas with sweet, anisic, ylang and geranium topnotes to perfume compositions, colognes and perfumed articles including soaps, bleaches, anionic, cationic, nonionic or zwitterionic detergents, fabric softener articles and other perfumed articles.

The process of our invention involves first reacting the compound having the structure:

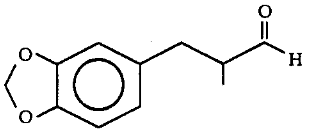

with a hydroxylamine acid salt having the formula:

$$[NH_3OH^{\oplus}]_M[X^{-m}]$$

wherein M is an integer selected from the group consisting of 1, 2 or 3 and X is defined, supra to form the novel compounds defined according to the structure:

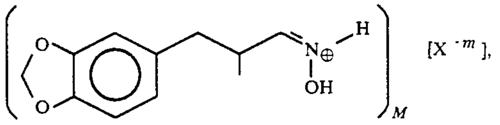

for example, the bisulfate salt having the structure:

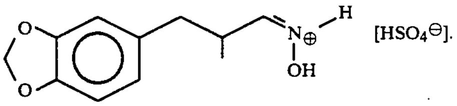

The resulting salt defined according to the structure:

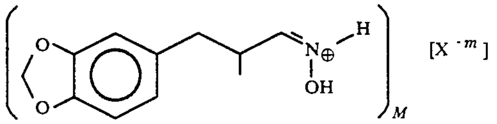

is then reacted with base, e.g., aqueous sodium hydroxide to form the hydroxylamine base defined according to the structure:

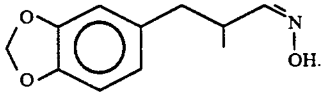

This material is in an of itself a perfumery substance, particularly when admixed with the material having the structure:

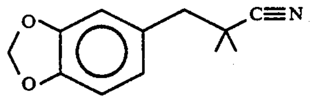

shown to be produced, infra.

The compound having the structure:

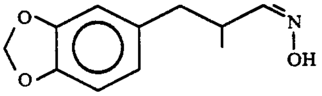

may then be reacted with the dehydrating agent, for example, cupric sulfate in combination with acetic anhydride to form the nitrile having the structure:

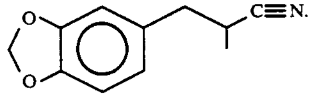

Thus, the reaction sequence for the foregoing two reactions is as follows:

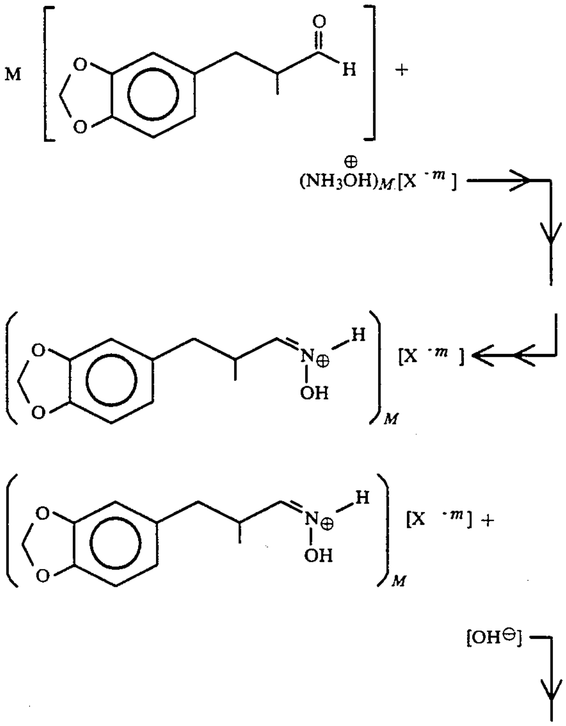

-continued

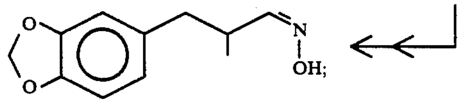

and

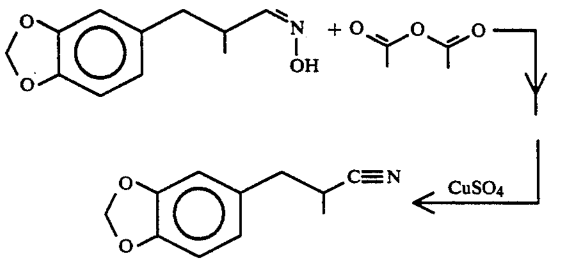

The compound having the structure:

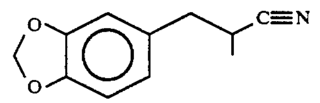

thus formed can be used as is for its perfumery properties or it can be further alkylated using methyl iodide in the presence of a lithium diisopropyl amide catalyst having the structure:

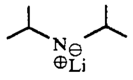

according to the reaction:

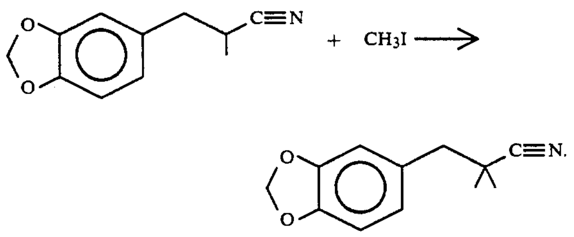

The resultant product is then crystallized and purified in accordance with standard practices for purification of a material which is solid at ambient conditions.

With reference to the reaction, to wit:

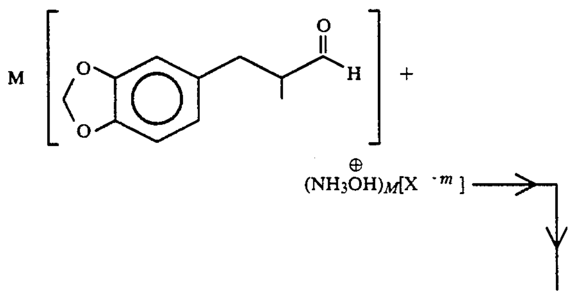

-continued

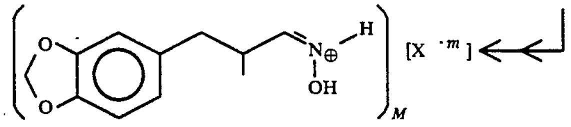

the reaction takes place in aqueous media at a temperature of between about 5° C. and about 10° C.

With reference to the reaction:

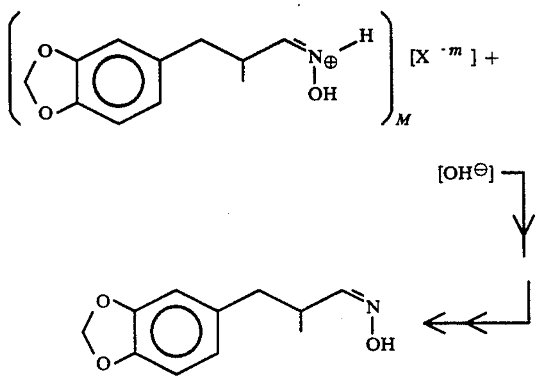

the reaction takes place in aqueous media using, for example, aqueous sodium hydroxide over a period of time of between about one and about three hours at a temperature of between about 35° C. and about 50° C. At the end of the reaction, the resulting product is crystallized and purified by standard purification techniques of materials which are solid at ambient conditions.

The reaction, to wit:

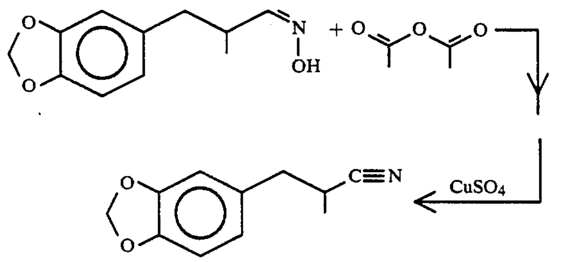

takes place at a temperature of between about 100° and 110° C. for a period of time of from about one up to about ten hours (preferably between about three and about seven hours). The dehydration reagent preferred in this reaction is a mixture of acetic anhydride and cupric sulfate. At the end of the reaction, the reaction product is fractionally distilled after appropriate "workup" and the fractional distillation of the compound having the structure:

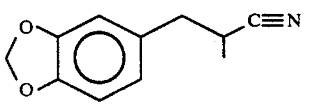

is at a vapor temperature of 130° C. and a vacuum of 1.55 mm/Hg.

The methylation reaction, to wit:

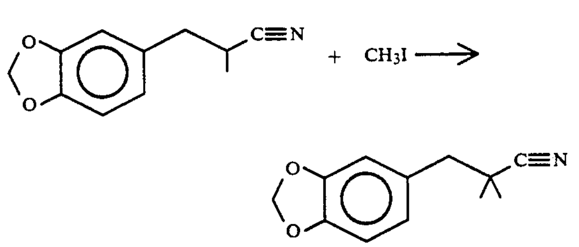

using methyl iodide takes place using preferably a lithium diisopropylamide catalyst having the structure:

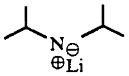

using preferably a solvent which is composed of tetrahydrofuran, ethyl benzene and heptane. The reaction takes place at a temperature in the range of from about 40° up to about 70° C. over a period of about three hours. At the end of the reaction, the reaction product having the structure:

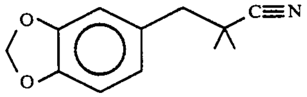

is crystallized and purified using standard purification procedures for materials which are crystalline at ambient conditions.

Perfumery use of the compound having the structure:

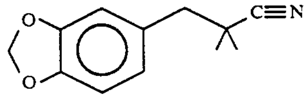

is either in solution, e.g., in diethyl phthalate solution or in admixture with other materials whereby a eutectic composition is formed, for example, in admixture with the compound having the structure:

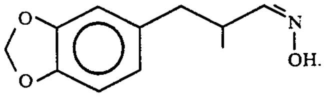

The high melting eutectic (68° C.) for the eutectic mixture of the compounds having the structures:

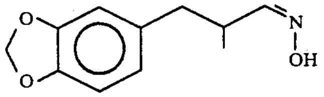

and

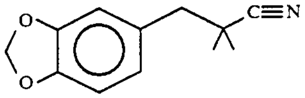

causes such mixture to be useful in bath oils where the higher temperature will bring out the intense anisic, floral, muguet and sweet aroma of such mixture.

The following table sets forth the perfumery properties of the various compositions of matter so useful in perfumery of our invention:

TABLE I

| Description of Composition | Perfumery Properties |
|---|---|
| Compound having the structure: 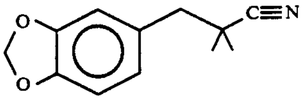 (50% solution in diethyl phthalate) prepared according to Example III. | A sweet, anisic, ozoney, ylang, geranium and melony aroma with sweet, anisic, ylang and geranium topnotes. |
| Compound having the structure: 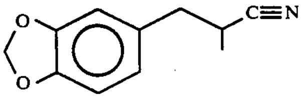 prepared according to Example II. | A sweet, basil aroma. |
| 75:25 (Weight:weight) mixture of compounds having the structure: 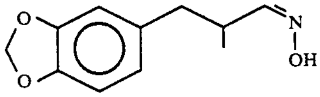 and 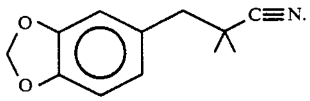 | An intense anisic, floral, muguet and sweet aroma profile (at 68° C.). |

The compounds having the structures:

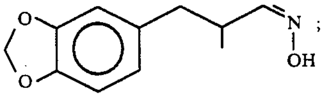

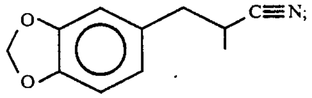

and

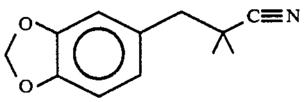

as well as mixtures thereof of our invention and one or more auxiliary perfume ingredients, including, for example, hydrocarbons, alcohols, ketones, aldehydes, nitriles (other than the nitriles of our invention), esters, lactones, ethers, hydrocarbons, synthetic essential oils and natural essential oils may be admixed so that the combined odors of the individual components produce a pleasant and desired fragrance particularly and preferably in the "pine fragrance" area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, at least one of the compounds having the structures:

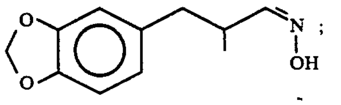

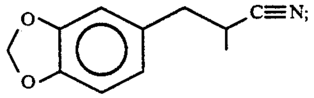

and

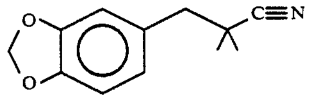

or mixtures thereof of our invention can be used to alter, modify or enhance the aroma characteristics of a perfume composition, for example, by utilizing or moderating the olfactory reaction contributed by another ingredient in the composition.

The amount of at least one of the compounds having the structures:

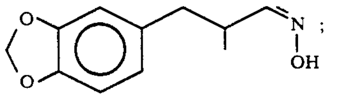

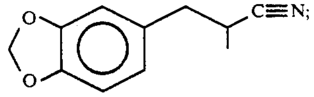

and

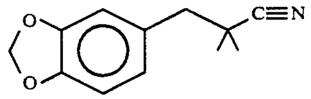

or mixtures thereof of our invention which will be effective in perfume compositions as well as in perfumed articles and colognes depends upon many factors, including the other ingredients, their amounts and the effects which are desired.

It has been found that perfume compositions containing as little as 0.05% of at least one of the compounds having the structures:

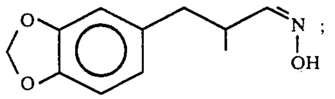

-continued

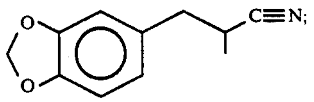

and

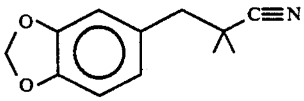

or mixtures thereof of our invention can be used to impart sweet, anisic, ozoney, ylang, geranium, melony, basil, floral and muguet aromas with sweet, anisic, ylang and geranium topnotes to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effects desired on the finished product and the particular fragrance sought.

At least one of the compounds having the structures:

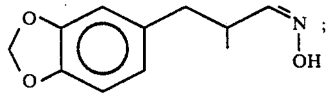

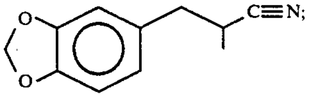

and

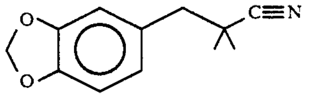

or mixtures thereof are useful (taken alone or together with other ingredients in perfume compositions), in detergents and soaps, space odorants and deodorants, perfumes, colognes, toilet water, bath preparations such as lacquers, brilliantines, pomades and shampoos; cosmetic preparations such as creams, deodorants, hand lotions and sun screens; powders, such as talcs, dusting powders, face powders and the like.

As little as 0.7% of at least one of the compounds havin the structures:

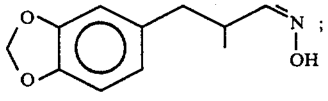

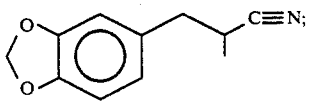

and

-continued

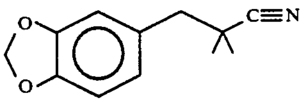

or mixtures thereof of our invention will suffice to impart an intense and substantive sweet, anisic, ozoney, ylang, geranium, melony, basil, floral and muguet aromas with sweet, anisic, ylang and geranium topnotes to pine perfume formulations. Generally, no more than 5% of at least one of the compounds having the structures:

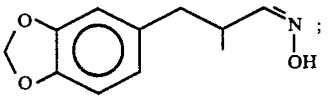

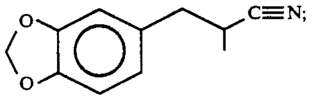

and

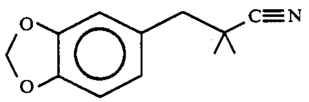

or mixtures thereof of our invention based on the ultimate end product is required to be used "as is" or in the perfume composition.

Furthermore, as little as 0.25% of at least one of the compounds having the structures:

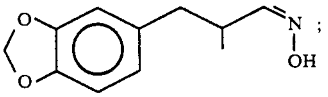

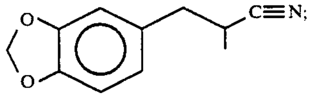

and

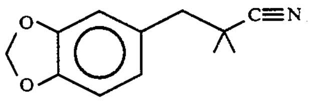

or mixtures thereof of our invention will suffice to impart such aroma to perfumed articles per se, whether in the presence of other perfume materials or whether used by themselves. Thus, the range of use of at least one of the compounds having the structures:

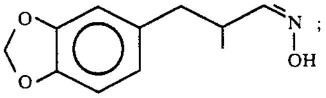

-continued

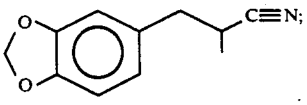

and

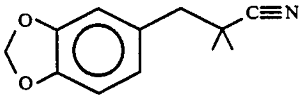

or mixtures thereof of our invention in perfumed articles may vary from about 0.25% up to about 5% by weight based on the total weight of the perfumed article.

In addition, the perfume composition or fragrance compositions of our invention can contain a vehicle, or carrier for at least one of the compounds having the structures:

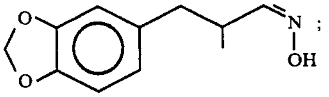

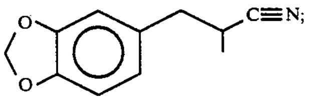

and

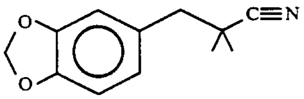

or mixtures thereof of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic), or components for encapsulating the composition as by means of coacervation (such as gelatin).

It will thus be apparent that at least one of the compounds having the structures:

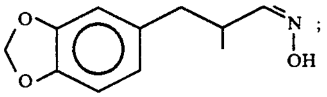

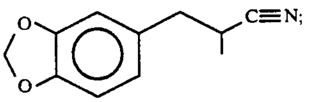

and

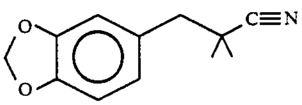

or mixtures thereof of our invention can be utilized to alter, modify or enhance the aroma of perfume composition, colognes or perfumed articles.

Furthermore, a number of processes known in the art and set forth, for example, in U.S. Pat. No. 5,143,899 issued on Sep. 1, 1992, the specification for which is incorporated by reference herein may be used in order to produce a thickened, highly viscous hypochlorite bleaching or sterilizing solution, whereby the desired aroma profiles are imparted to the articles treated with such hypochlorite solutions. Specifically, the disclosure set forth at columns 12, 13, 14, 15, 16, 17 and 18 of said U.S. Pat. No. 5,143,899 is incorporated by reference herein.

The following Examples I, II and III serve to illustrate processes for preparing the p-methylenedioxyphenyl propionitrile and propiohydroxylamine derivatives of our invention.

Examples following Example III in general serve to illustrate the organoleptic utilites of the compounds having the structures:

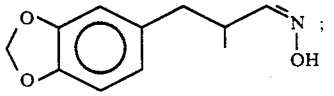

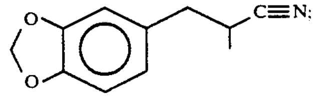

and

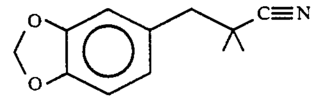

or mixtures thereof of our invention.

In general, the following examples serve to illustrate specific embodiments of our invention. It will be understood that these examples are illustrative and that the invention is to be considered restricted thereto only as indicated in the appended claims.

All parts and percentages given herein are by weight unless otherwise specified.

EXAMPLE I

Preparation of Alpha-Methyl-3,4-(Methylene Dioxy) Hydrocinnamaldehyde Oxime

Reactions

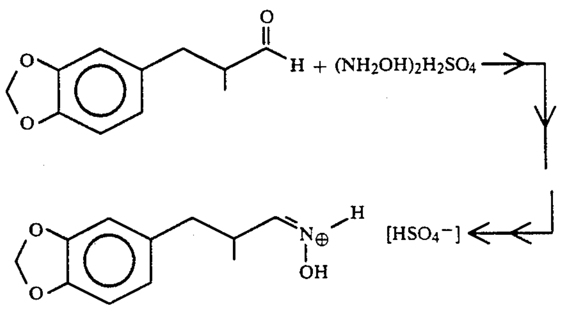

and

-continued

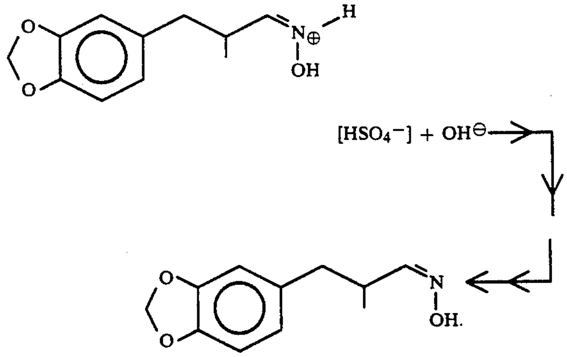

Into a 12 liter reaction vessel equipped with stirrer, thermometer, cooling coils and heating mantle as well as reflux condenser are placed a mixture of 2500 ml water and 1179 grams (7.14 moles) of hydroxylamine sulfate. The resulting mixture is stirred until homogeneous. Over a period of five minutes while maintaining the reaction mass at 7° C., the compound having the structure:

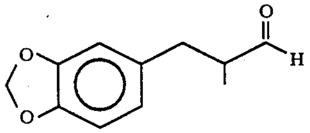

in an amount of 1600 grams (10 moles) is added to the reaction mass. The reaction mass is stirred for a period of about five minutes. The compound having the structure:

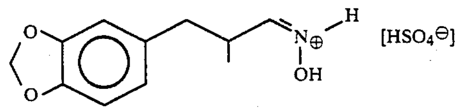

is thus formed.

Over a period of two hours, 1314 grams of 50% aqueous sodium hydroxide (containing 657 grams of solid sodium hydroxide) is added to the reaction mass. The reaction mass exotherms to 42° C. and is maintained at between 38 and 42° C. for a period of three hours (with stirring).

The reaction mass now exists in two phases; an aqueous phase and an organic phase. Two liters of methylene dichloride is added to the reaction mass.

The organic phase is now separated from the aqueous phase and the organic phase is washed with two 1000 ml portions of saturated sodium chloride and then dried over anhydrous magnesium sulfate. The resulting product is filtered and then cooled and the product having the structure:

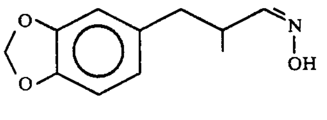

is isolated in the form of crystals (yield:1420 grams). The structure of the resulting product is confirmed by NMR and IR analyses as set forth in the description of FIGS. 2 and 3, supra.

The resulting product when mixed in a 75:25 weight (weight:weight) ratio with the compound having the structure:

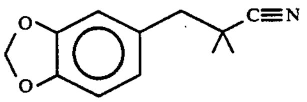

has an intense anisic, floral, muguet and sweet aroma profile. The resulting compound forms a eutectic mixture with the compound having the structure:

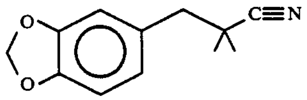

at 68° C. as shown in FIG. 10 described, supra. The liquid-solid phase boundary of various mixtures of the compound having the structure:

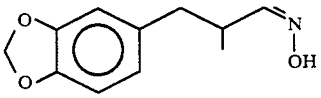

and the compound having the structure:

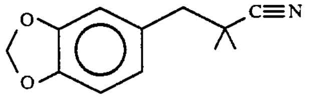

are set forth in FIG. 10 with the graph showing the boundary between the solid and liquid phases being indicated by reference numeral 100. The area showing the solid phase is indicated by reference numeral 104 and the area showing the liquid phase is indicated by reference numeral 102. The eutectic point at 68° C. is indicated by reference numeral 106. The 75:25 (weight:-weight) mixture of the compound having the structure:

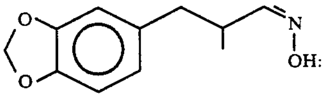

the compound having the structure:

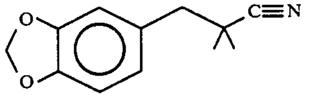

exists at 80° C. and it, too, has an intense anisic, floral, muguet and sweet aroma. This mixture is particularly useful in bath oils used in hot baths where the aroma is particularly striking, intense and substantive. Thus, the use in hot bath oils is of particular interest for such mixtures.

EXAMPLE II

Preparation of Alpha-Methyl-3,4-(Methylenedioxy) Hydrocinnamonitrile

Reaction

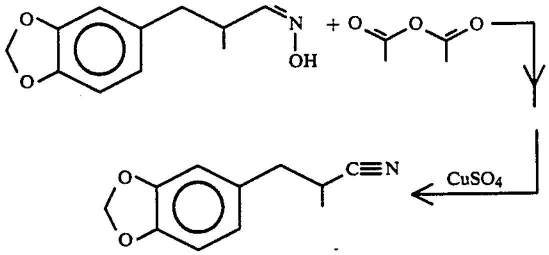

Into a 5 liter reaction flask equipped with stirrer, thermometer, reflux condenser and heating mantle are placed 963 grams (9.44 moles) of acetic anhydride and 6 grams of cupric sulfate. The resulting mixture with stirring is heated to 100° C. While maintaining the reaction mass at 100° C., over a period of three hours, 1303 grams (6.29 moles) of the compound having the structure:

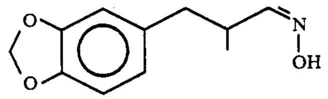

is added to the reaction mass. The reaction mass is then stirred for a period of six hours while maintaining the temperature thereof at 100° C.

The reaction mass is then quenched with 2 liters of water reducing the temperature of the mixture to 30° C.

The reaction mass now exists in two phases; an organic phase and an aqueous phase. The aqueous phase is extracted with 300 ml toluene and the toluene extract is combined with the organic phase. The resulting organic phase is then washed with 1000 ml water followed by 500 ml of a 10% aqueous sodium bicarbonate solution followed by 500 ml of a saturated sodium chloride solution.

The resulting product is then filtered through anhydrous magnesium sulfate and distilled through a fractionation column yielding the following fractions:

| Fraction No. | Vapor Temp. (°C.) | Liquid Temp. (°C.) | Vacuum mm/Hg. Pressure |
|---|---|---|---|
| 1 | 27/42 | 48/82 | 100/2.56 |
| 2 | 130 | 140 | 1.55 |
| 3 | 110 | 200 | 1.62. |

Fraction 2 is the material which has the structure:

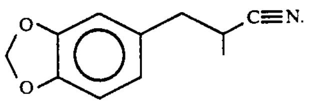

This compound has a sweet, basil aroma. The structure of the compound, to wit:

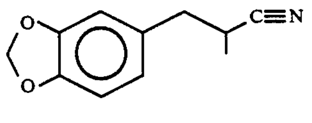

is confirmed by NMR and IR analyses as set forth in the description of FIGS. 5 and 6, supra.

EXAMPLE III

Preparation of Alpha,Alpha-Dimethyl-3,4-(Methylenedioxy) Hydrocinnamonitrile

Reaction

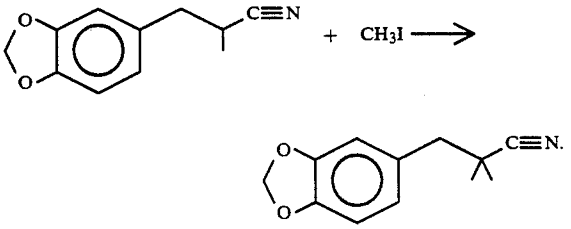

Into a 5 liter reaction flask equipped with cooling oils, thermometer, reflux condenser and heating mantle are placed 2.0 moles of lithium diisopropyl amide having the structure:

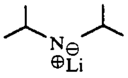

in a solvent which is a mixture of tetrahydrofuran, ethyl benzene and heptane. The resulting mixture is cooled to 0° C. Over a period of one hour while maintaining the temperature at between 0° and 5° C., 630 grams (3.2 moles) of the compound having the structure:

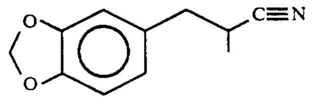

produced according to Example II is added to the reaction mass with stirring. The reaction mass is cooled to 0° C. and stirred for a period of 0.5 hours. At the end of the 0.5 hour period, over a period of one hour, 691 grams (4.87 moles) of methyl iodide is added to the reaction mass. The reaction mass is stirred at 60° C. for a period of three hours; and then cooled to 35° C. The reaction mass is then quenched with 1 liter of 2 molar hydrochloric acid. The reaction mass is then admixed with 400 ml concentrated hydrochloric acid. The reaction mass now exists in two phases; an aqueous phase and an organic phase. The organic phase is washed with 2000 ml water followed by 500 ml 10% aqueous sodium bicarbonate followed by 500 ml saturated sodium chloride solution. The reaction mass is then filtered through anhydrous magnesium sulfate and distilled to yield 285 grams of product, through a fractionation column yielding the following fractions:

| Fraction No. | Vapor Temp. (°C.) | Liquid Temp. (°C.) | Vacuum mm/Hg. Pressure |
|---|---|---|---|
| 1 | 45/ | 112/ | 4.90/ |
| 2 | 147/130 | 152/200 | 3.56/9.08. |

The resulting product crystallizes. The structure, to wit:

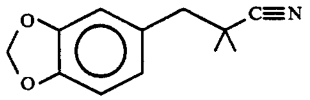

is confirmed via NMR and IR analyses as shown in FIGS. 8 and 9.

A 50% solution of the resulting product in diethyl phthalate has a sweet, anisic, ozoney, ylang, geranium and melony aroma with sweet, anisic, ylang and geranium topnotes.

EXAMPLE IV

The following Chypre formulations are prepared:

| Ingredients | Parts by Weight IV(A) | IV(B) | IV(C) |
|---|---|---|---|
| Musk ambrette | 40 | 40 | 40 |
| Musk ketone | 60 | 60 | 60 |
| Coumarin | 30 | 30 | 30 |
| Oil of bergamot | 150 | 150 | 150 |
| Oil of lemon | 100 | 100 | 100 |
| Methyl ionone | 50 | 50 | 50 |
| Hexyl cinnamic aldehyde | 100 | 100 | 100 |
| Hydroxycitronellal | 100 | 100 | 100 |
| Oil of lavender | 50 | 50 | 50 |
| Texas cedarwood oil | 85 | 85 | 85 |
| Virginia cedarwood oil | 30 | 30 | 30 |
| Oil of sandalwood (East Indies) | 40 | 40 | 40 |
| Eugenol | 10 | 10 | 10 |
| Benzyl acetate | 30 | 30 | 30 |
| alpha-Phenyl ethyl alcohol | 40 | 40 | 40 |
| beta-Phenyl ethyl alcohol | 30 | 30 | 30 |
| Oakmoss absolute | 30 | 30 | 30 |
| Vetiver oil Venezuela | 25 | 25 | 25 |
| The compound having the structure: 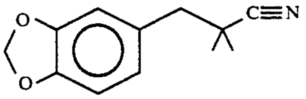 (50% in diethyl phthalate) prepared according to Example III. | 62 | 0 | 0 |
| The compound having the structure: 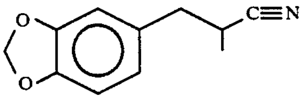 prepared according to Example II. | 0 | 62 | 0 |
| A 75:75 (weight:weight) mixture of the compound having the structure: 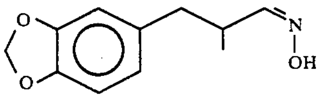 and the compound having the structure: | 0 | 0 | 62 |

-continued

| Ingredients | Parts by Weight IV(A) | IV(B) | IV(C) |
|---|---|---|---|
| 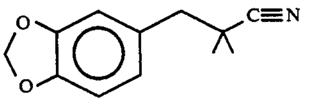 | | | |

The compound having the structure:

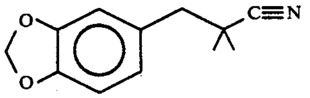

(50% in diethyl phthlate) prepared according to Example III imparts to this Chypre formulation sweet, anisic, ozoney, ylang, geranium and melony undertones with sweet, anisic, ylang and geranium topnotes. Accordingly, the Chypre formulation of Example IV(A) can be described as "a Chypre aroma with sweet, anisic, ozoney, ylang, geranium and melony undertones and sweet, anisic, ylang and geranium topnotes".

The compound having the structure:

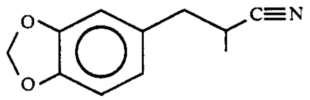

prepared according to Example II imparts to this Chypre formulation intense and substantive sweet and basil undertones. Accordingly, the Chypre formulation of Example IV(B) can be described as having "a Chypre aroma with sweet and basil undertones".

The mixture of compounds having the structures:

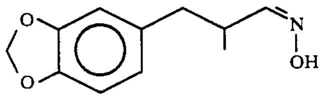

and

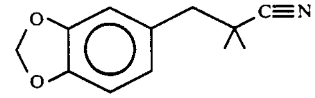

(75:25 weight:weight) imparts to this Chypre formulation intense anisic, floral, muguet and sweet undertones. Accordingly, the perfume composition of Example IV(C) can be described as having "a Chypre aroma with intense anisic, floral, muguet and sweet undertones".

EXAMPLE V

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 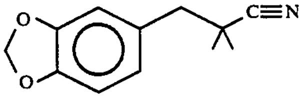 (50% in diethyl phthalate) prepared according to Example III. | A sweet, anisic, ozoney, ylang, geranium and melony aroma with sweet, anisic, ylang and geranium topnotes. |
| The compound having the structure: 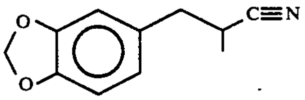 prepared according to Example II. | A sweet and basil aroma. |
| 75:25 (Weight:weight) mixture of compounds having the structures: 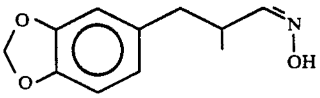 and 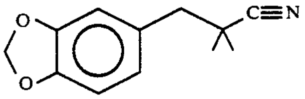 | An intense anisic, floral, muguet and sweet aroma profile. |
| Perfume composition of Example IV(A). | A Chypre aroma with sweet, anisic, ozoney, ylang, geranium and melony undertones and sweet, anisic, ylang and geranium topnotes. |
| Perfume composition of Example IV(B). | A Chypre aroma with sweet and basil undertones. |
| Perfume composition of Example IV(C). | A Chypre aroma with intense anisic, floral, muguet and sweet undertones. |

EXAMPLE VI

Perfumed Liquid Detergent

Concentrated liquid detergents (Lysine slat of n-dodecylbenzene sulfonic acid as more specifically described in U.S. Pat. No. 3,948,818 issued on Apr. 6, 1976) with aroma nuances as set forth in Table II of Example V are prepared containing 0.10%, 0.15%, 0.20%, 0.25%, 0.30% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentration of substance set forth in Table II of Example V.

EXAMPLE VII

Preparation of Colognes and Handkerchief Perfumes

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

Preparation of Soap Compositions

One hundred grams of soap chips [per sample] IVORY ®, produced by the Procter & Gamble Company of Cincinnati, Ohio), are each mixed with one gram samples of substances as set forth in Table II of Example V until homogeneous compositions are obtained. In each of the cases, the homogeneous compositions are heated under 8 atmospheres pressure at 180° C. for a period of three hours and the resulting liquids are placed into soap molds. The resulting soap cakes, in cooling, manifest aromas as set forth in Table II of Example V.

EXAMPLE IX

Preparation of Solid Detergent Compositions

Detergents are prepared using the following ingredients according to Example I of Canadian Patent No. 1,007,948:

| | |
|---|---|
| "NEODOL ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396, non-woven cloth substrates useful as drier-added fabric softening articles of manufacture are prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57%—$C_{20-22}$ HAPS;
   22%—isopropyl alcohol;
   20%—antistatic agent;
   1%—of one of the substances as set forth in Table II of Example V.

Fabric softening compositions prepared according to Example I at column 15 of U.S. Pat. No. 3,632,396 having aroma characteristics as set forth in Table II of Example V, consist of a substrate coating having a weight of about 3 grams per 100 square inches of substrate; a first coating on the substrate coating consisting of about 1.85 grams per 100 square inches of substrate; and outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example V.

EXAMPLE XI

Hair Spray Formulations

The following hair spray formulation is prepared by first dissolving PVP/VA E-735 a copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| TWEEN ® surfactant (prepared by ICI America Corporation) | 0.03 |
| One of the perfumery substances as set forth in Table II of Example V | 0.10 |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

Conditioning Shampoos

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT ® polymer (manufactured by GAF Corporation of 140 West 51st Street, New York, N.Y.)(5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

EXAMPLE XIII

Four drops of each of the substances set forth in Table II of Example V, supra, is added separately to two grams of AROMOX® DMC-W to produce a clear premix. The clear premix is added to 200 grams of CLOROX® with stirring resulting in a clear stable, single phase solution. sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II of Example V. Furthermore, no such characteristic "hypochlorite" aroma is retained on the hands of the individual handling such laundry in both the wet and the dry states.

EXAMPLE XIV

AROMOX® DMMC-W in various quantities is mixed with 0.1 grams of one of the substances set forth in Table II of Example V, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table II of Example V. Furthermore, no such characteristic "hypochlorite" aroma is retained on the hands of the individual handling such laundry in both the wet and dry states.

What is claimed is:

1. The process for preparing the compound having the structure:

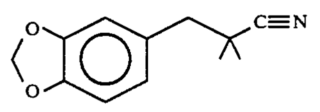

comprising the steps of:

(i) reacting the compound having the structure:

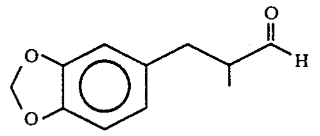

with a compound having the structure:

$[NH_3OH^{\oplus}]_M[X^{-m}]$ according to the reaction:

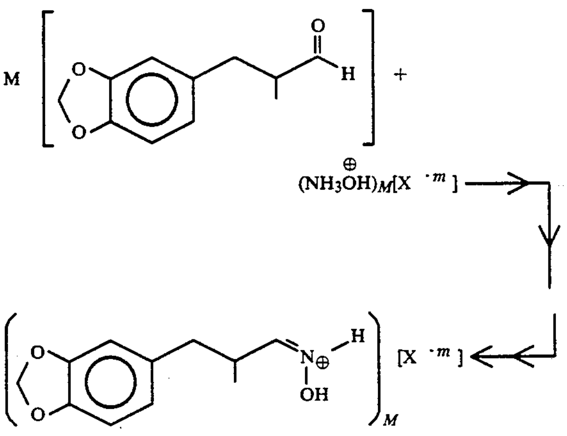

(ii) then reacting the compound thus formed having the structure:

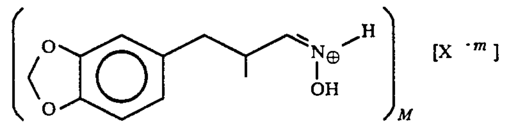

with base according to the reaction:

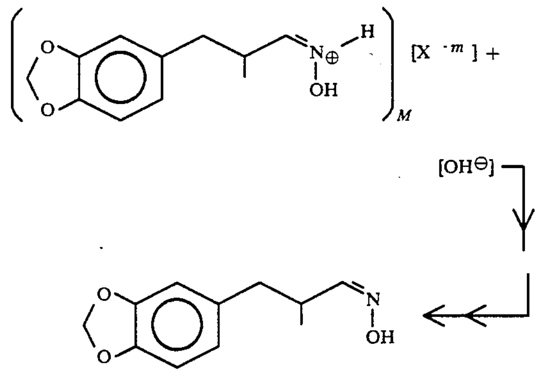

(iii) then reacting the thus formed compound having the structure:

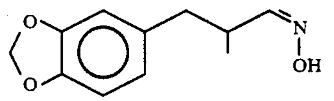

with a cupric sulfate-acetic anhydride mixture according to the reaction:

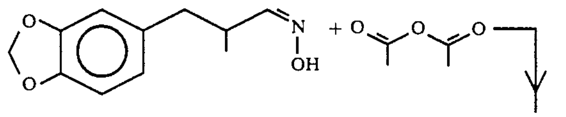

-continued

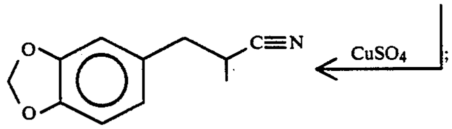

;

(iv) then reacting the resulting product having the structure:

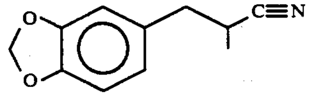

with methyl iodide in the presence of a lithium diisopropylamide catalyst having the structure:

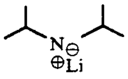

according to the reaction:

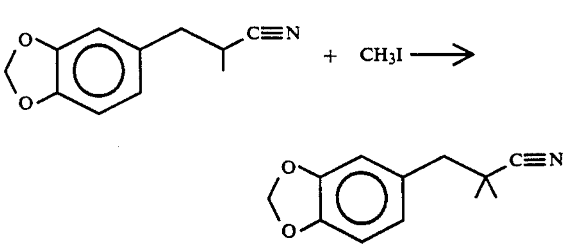

wherein X is an anion selected from the group consisting of:
$HSO_4^-$;
$SO_4^=$;
$Cl^-$;
$Br^-$;
$PO_4^{\equiv}$;
$H_2PO_4^-$; and
$HPO_4^=$
and M is an integer selected from the group consisting of 1, 2 and 3.

* * * * *